(12) United States Patent
Cornil et al.

(10) Patent No.: US 8,556,887 B2
(45) Date of Patent: Oct. 15, 2013

(54) LASER BEAM DERMATALOGICAL HEAT TREATMENT DEVICE

(75) Inventors: Alain Cornil, Aix en Provence (FR); Alban Gosse, Mimet (FR); Patrick Peronne, Paris (FR)

(73) Assignee: Vivatech, Paris (FR)

( * ) Notice: Subject to any disclaimer, the term of this patent is extended or adjusted under 35 U.S.C. 154(b) by 770 days.

(21) Appl. No.: 12/745,020

(22) PCT Filed: Dec. 3, 2008

(86) PCT No.: PCT/EP2008/066729
§ 371 (c)(1),
(2), (4) Date: May 27, 2010

(87) PCT Pub. No.: WO2009/071592
PCT Pub. Date: Jun. 11, 2009

(65) Prior Publication Data
US 2010/0305554 A1    Dec. 2, 2010

(30) Foreign Application Priority Data
Dec. 3, 2007    (FR) ...................................... 07 59521

(51) Int. Cl.
*A61B 18/18*    (2006.01)
(52) U.S. Cl.
USPC ............................................................. 606/9
(58) Field of Classification Search
USPC ...................................................... 606/7–9
See application file for complete search history.

(56) References Cited

U.S. PATENT DOCUMENTS

| 5,595,568 | A | 1/1997 | Anderson et al. |
| 5,630,811 | A | 5/1997 | Miller |
| 5,735,844 | A | 4/1998 | Anderson et al. |
| 5,755,753 | A | 5/1998 | Knowlton |
| 2002/0138119 | A1 | 9/2002 | Angeley et al. |
| 2007/0179571 | A1* | 8/2007 | De Taboada et al. ........... 607/88 |

FOREIGN PATENT DOCUMENTS

| EP | 0 265 470 B1 | 9/1992 |
| EP | 1 354 573 A1 | 10/2003 |
| EP | 1 744 349 A2 | 1/2007 |
| EP | 1 748 471 A1 | 1/2007 |
| WO | 98/51235 A1 | 11/1998 |
| WO | 00/53114 A1 | 9/2000 |

OTHER PUBLICATIONS

International Search Report, dated Mar. 9, 2009, from corresponding PCT application.

* cited by examiner

*Primary Examiner* — James Greece
(74) *Attorney, Agent, or Firm* — Young & Thompson

(57) ABSTRACT

A device for dermatological treatment, includes an energy source, the energy source generating a quasi-Gaussian laser beam, characterized in that it includes an element for shaping the beam between the energy source and a source to be treated, the shaping element being adapted for converting the beam into a beam having a power distributed homogenously on a given surface, and in that the device further includes a removable and replaceable optical unit.

25 Claims, 10 Drawing Sheets

LASER BEAM DERMATALOGICAL HEAT TREATMENT DEVICE

This invention relates to the treatment of a patient's skin wounds with a laser beam, and more specifically a device for such treatment.

Various solutions for promoting wound healing by using an external energy source are known in the current state of the art. They consist of treating the tissue with light energy emitted by a laser source in order to selectively heat specific parts of the skin, during a very short laser firing time (less than one second). The selective nature of the treatment means temperature increases in the irradiated tissue areas are restricted.

The wavelength of the laser beams is chosen according to the area to be treated. In laser hair removal, the wavelength corresponds to the absorption peaks of melanin, the main constituent of the hair bulb.

The laser acts by producing a laser light pulse that is selectively absorbed by the lesion to be treated, on the basis of its colour, without damaging the surrounding tissue.

European patent application EP265470 also describes a device which is used for uniting the lips of a wound comprising a laser the emission wavelength of which is chosen such that it can perform tissue bonding and unite the lips of the wound, and a holding piece suitable for being secured to the tissue around the wound so as to hold the lips of said wound in contact, at least while the wound is exposed to said laser radiation.

The key idea is to unite both skin and vessels, by using sufficient laser energy to achieve an increase in tissue temperature beyond 60° C., suitable for denaturing and achieving interdigitation of the collagen fibres. This temperature is currently acknowledged to be the level above which irreversible heat damage is caused if tissue is heated for longer than one second, leading to tissue coagulation and necrosis through burning which slows and reduces the quality of the healing process.

In general, the prior art aims to apply electromagnetic energy emitted by a laser or radio frequency (RF) source to the tissue such as to selectively heat specific parts of the skin, with a variety of different approaches:

For techniques targeting small structures, the irradiation times are very short, less than the thermal relaxation time in the targeted zone. This is the case for hair removal systems and the treatment of vascular lesions. In both cases, the laser beam wavelength is selected according to the area to be treated. In laser hair removal, the wavelength corresponds to the absorption peaks of melanin, which is the main constituent of the hair bulb (documents U.S. Pat. Nos. 5,595,568 and 5,735,844). Vascular laser treatment involves a wavelength selected for maximum absorption by the haemoglobin.

For deep structures (the dermis for example): the principle of selectivity is achieved by combining the RF or laser source with a surface cooling system that reverses the temperature gradient, thus preserving the surface structures. This is the case in RF (document U.S. Pat. No. 5,755,753) or laser remodelling techniques.

A third approach to selectivity combines both solutions and can also be used in conjunction with pressure that is applied to reduce the quantity of blood and hence of haemoglobin, which could interfere with the treatment, in the skin (document U.S. Pat. No. 5,630,811).

To conclude, in the prior art, the use of a laser beam, which generally has a conventional Gaussian profile, has a major disadvantage. The energy distribution is similar to that of a Gaussian function, with the direct consequence of heating the skin surface in a non-uniform and selective manner, with a major temperature peak in the centre of the irradiated zone, which would cause a temperature gradient that is too great with respect to the precision of the temperature range in which it is desirable to operate.

One aim of the present invention is to seek to improve the prior art in order to solve the aforementioned problem.

To this end the invention embodies a dermatological treatment device comprising an energy source, the energy source emitting a quasi-Gaussian laser beam, characterised by the fact that it includes a means of shaping the beam between the energy source and the zone to be treated, the means of shaping being suitable for converting the beam into a beam, the power of which is distributed homogeneously over a given area, and by the fact that in addition the device includes a detachable and interchangeable optical unit.

This homogeneous distribution of power is used to achieve selective yet overall and homogeneous heating across the tissue area to be treated, in order to activate tissue healing processes.

Advantageously but optionally, the invention includes at least one of the following features:

- the means used to shape the laser beam are suitable for converting the beam into a beam with a flat-top profile.
- the means used to shape the laser beam include at least one lens array and one cylindrical lens.
- the device includes an optical fibre placed in front of the energy source in order to reduce the divergence of the energy source fast axis.
- the device includes a means of pyrometry.
- the device includes a user interface including at least one of the following components: an LCD screen, an emergency stop button, a on/off button, a double button system, an indicator light and a buzzer.
- the energy source is a diode, the wavelength of which is between 800 and 1,800 nm, and preferably between 810 nm and 910 nm.
- the device includes a means of energy storage (battery) for autonomous operation.
- the device includes an RFID (Radio Frequency Identification) reader in order to ensure the device can be safely used.
- the range of the RFID reader is less than 5 mm.
- the device includes a microcontroller for managing the energy source.
- the device includes a recess, positioned downstream of the output from the laser beam shaper in order to ensure there is a distance between the shaping device output and the treatment zone.

The invention also relates to a treatment kit comprising a device as claimed in the invention, and which additionally includes a sterilisation sleeve.

The invention also relates to a sterilisation sleeve.

The invention also relates to a dermatological treatment device and a dermatological treatment process whereby:

- the dermatological treatment device includes a device as claimed in the invention and an RFID component, the RFID component being designed to transmit information about the treatment zone to the device.
- the device includes a microcontroller for managing the process by which the RFID component is read.
- the RFID component interacts with the energy source by means of a contact.
- the operating settings of the energy source are memorised in the RFID component and communicated to the energy source control device.

the RFID component includes a means of storing information characterising a status of the area to be treated, the information corresponding to one of the following statuses:
  the area to be treated has not been treated.
  the area to be treated is in the course of treatment.
  treatment of the area to be treated has finished.
the RFID component operates at frequency of between 13 and 14 MHz.
the device, receiving information about the status of the zone to be treated, has a means of preventing the reuse of the adhesive element containing an RFID component when this has already been used once to treat the treatment zone.
the RFID (92) component is contained in an adhesive element (90), the adhesive element (92) being positioned close to the area to be treated.
the RFID component includes a means of preventing the reuse of the adhesive element if this has already been used to treat a treatment area.
the RFID (92) component being included in the sterilising sleeve.
the RFID (92) component being included in a portable element.
the portable element is chosen from the following group: nametag, telephone, bleeper, id card.

The invention also relates to a dermatological treatment process, whereby:
  the process is preferably suitable for biochemical activation of the healing of a patient's skin wounds, using a treatment device as claimed in the invention, and whereby the process includes a stage in which a laser beam is applied to an area of the said patient's skin, and whereby the power of the said beam is distributed homogeneously across the whole area.
  in addition, the process includes the following prior step:
    the treatment device is placed in a sterilising sleeve.
  in addition, the process includes the following steps:
    affixing an adhesive element in the vicinity of the zone to be treated.
    selecting an optical unit for the device.
    bringing the device close to the wound so that the RFID reader can read information from the RFID component.
    applying the laser beam to the area to be treated.

Further characteristics, aims and advantages of this invention will become clear through reading the detailed description below and referring to the drawings appended hereto, given by way of non-exhaustive examples and wherein.

Figure 6:
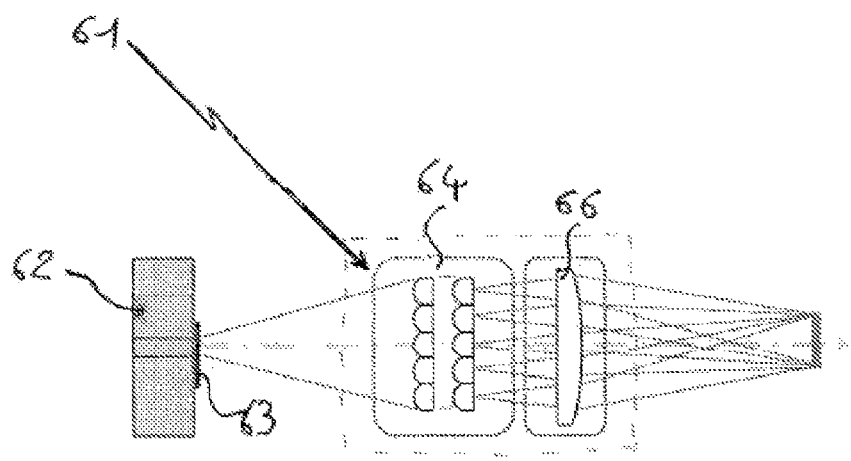

FIG. 6 gives a schematic illustration of a laser beam conversion device as claimed in the invention.

Figure 7:
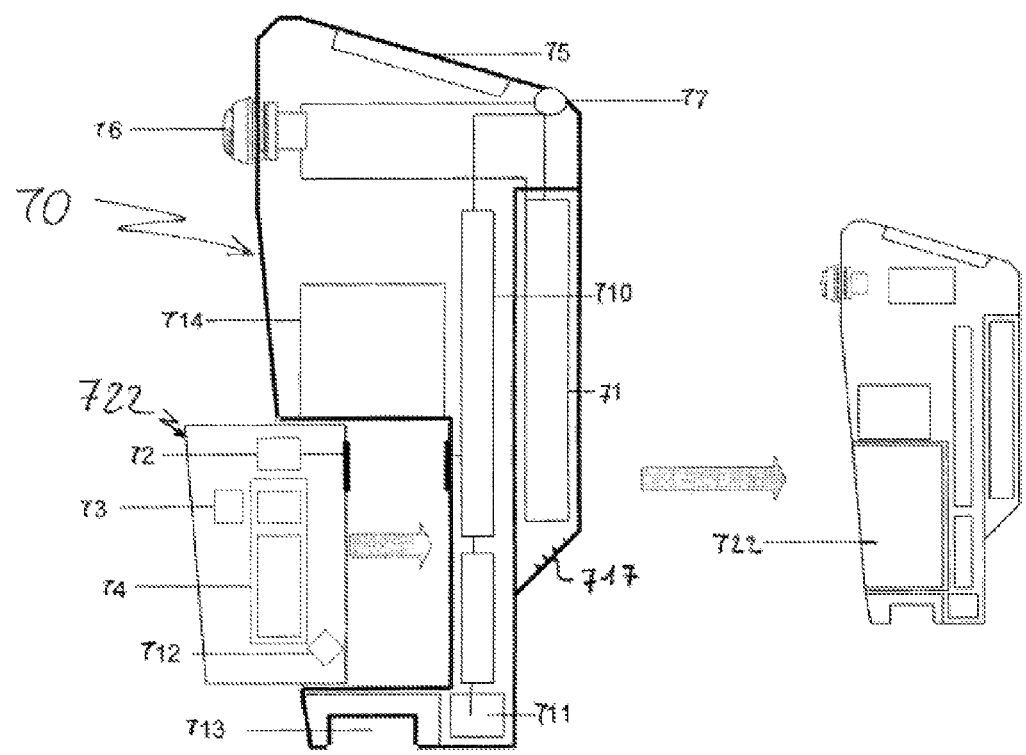
Figure 8:
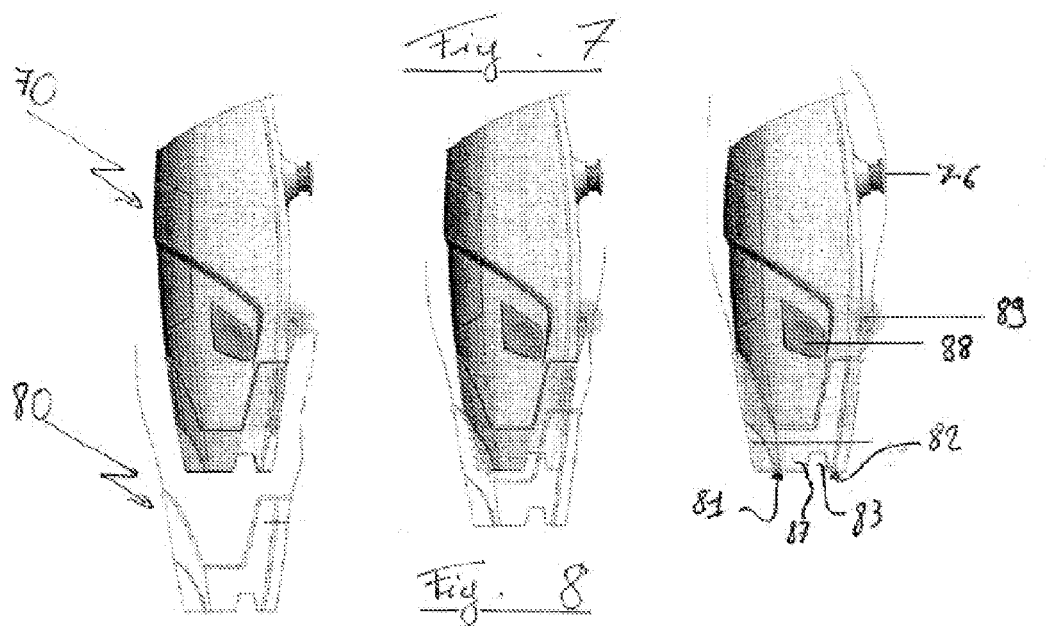

FIGS. 7 and 8 are diagrams illustrating a dermatological treatment device as claimed in the invention.

Figure 9:
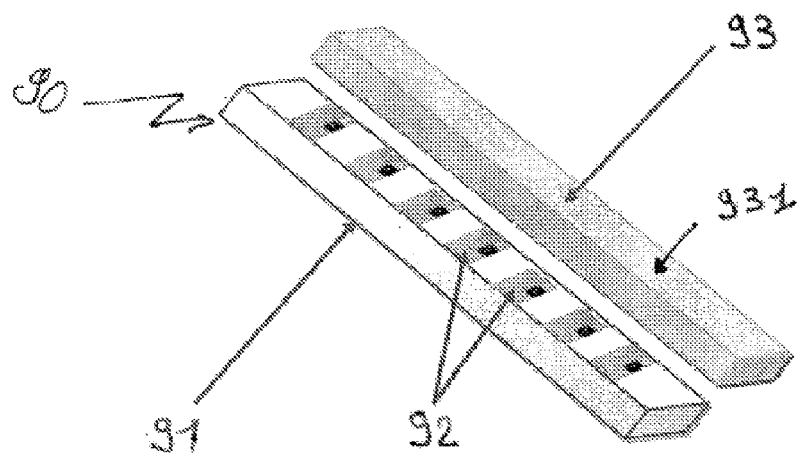

FIG. 9 is a simplified diagram of a skin closure strip as claimed in the invention.

Figure 10:
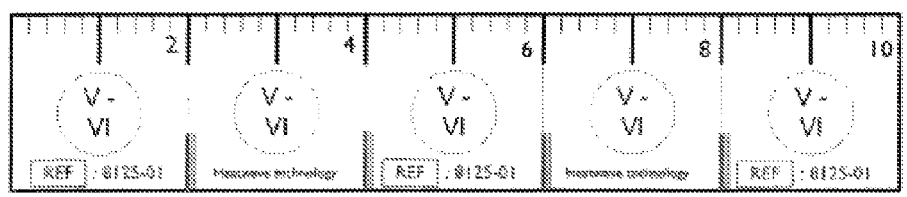

FIG. 10 illustrates the design that could be printed on a skin closure strip as claimed in the invention.

Figure 11:
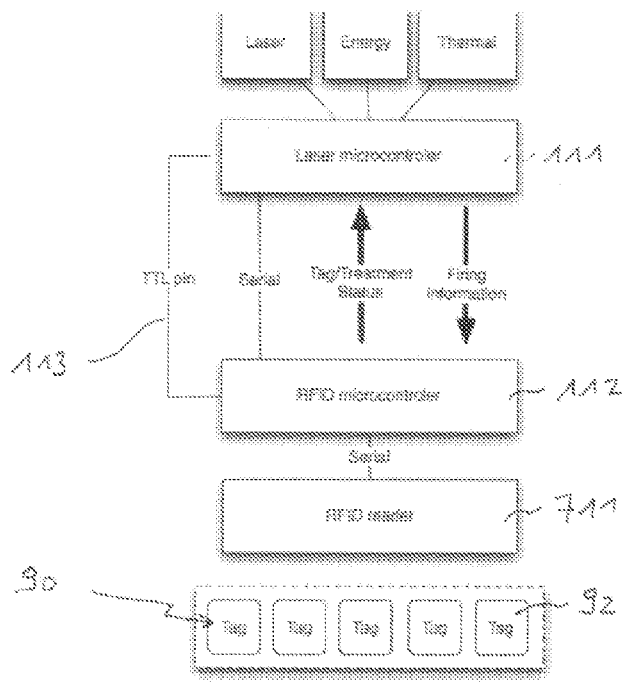

FIG. 11 is a schematic representation of the communications between an RFID component and the two microcontrollers in a device as claimed in the invention.

Figures 12A, 12B, 12C:
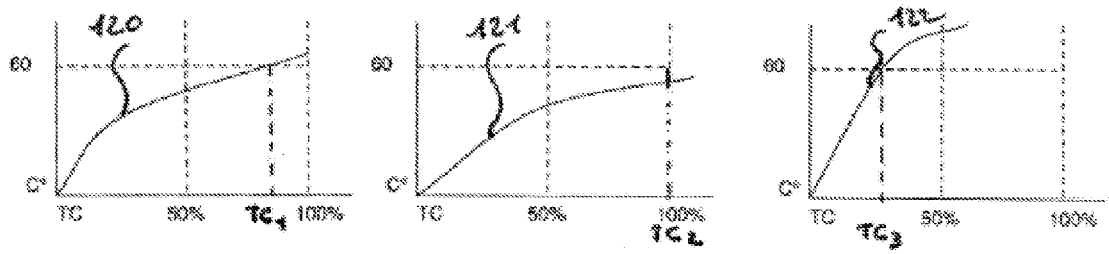

FIGS. 12a to 12c are graphs illustrating various temperature increase scenarios on the surface of an area of treated tissue.

Figure 13:
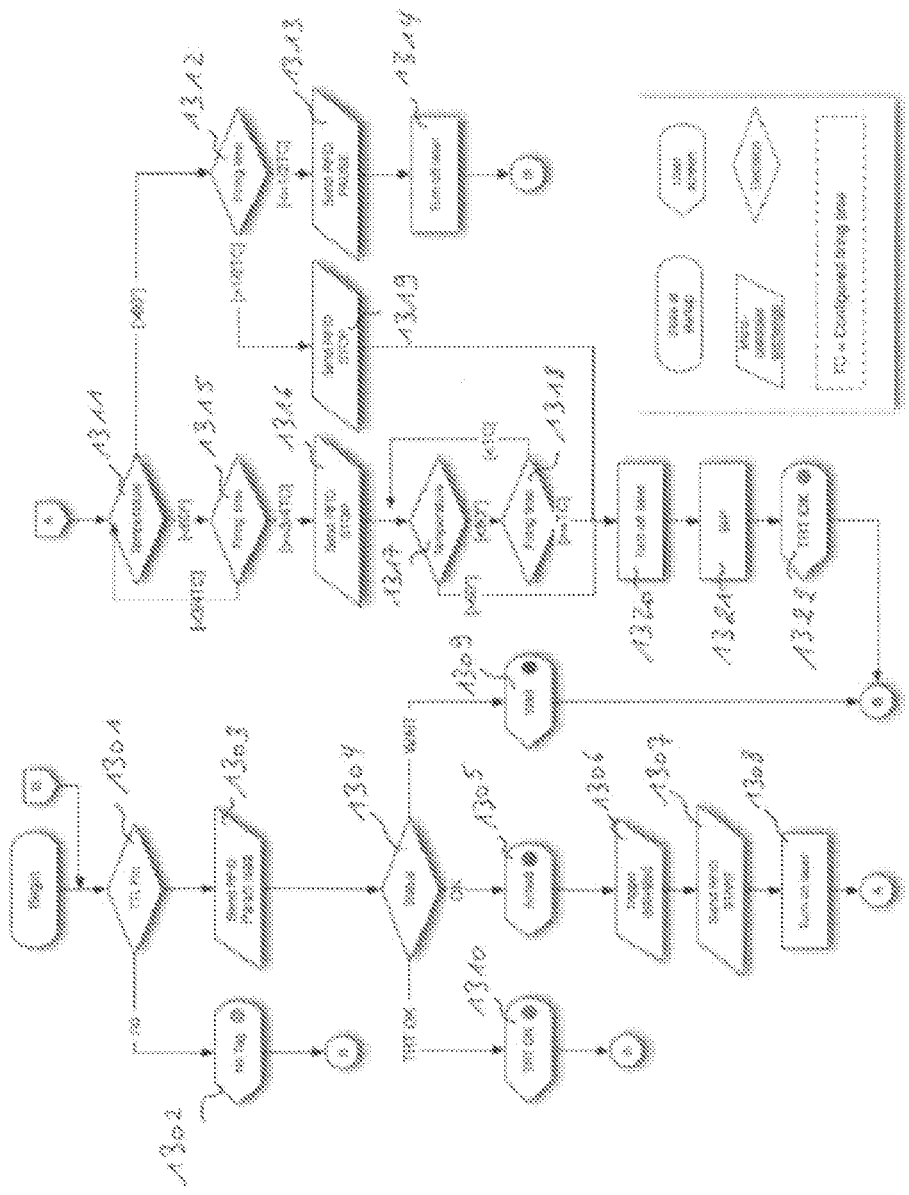
Figure 14:
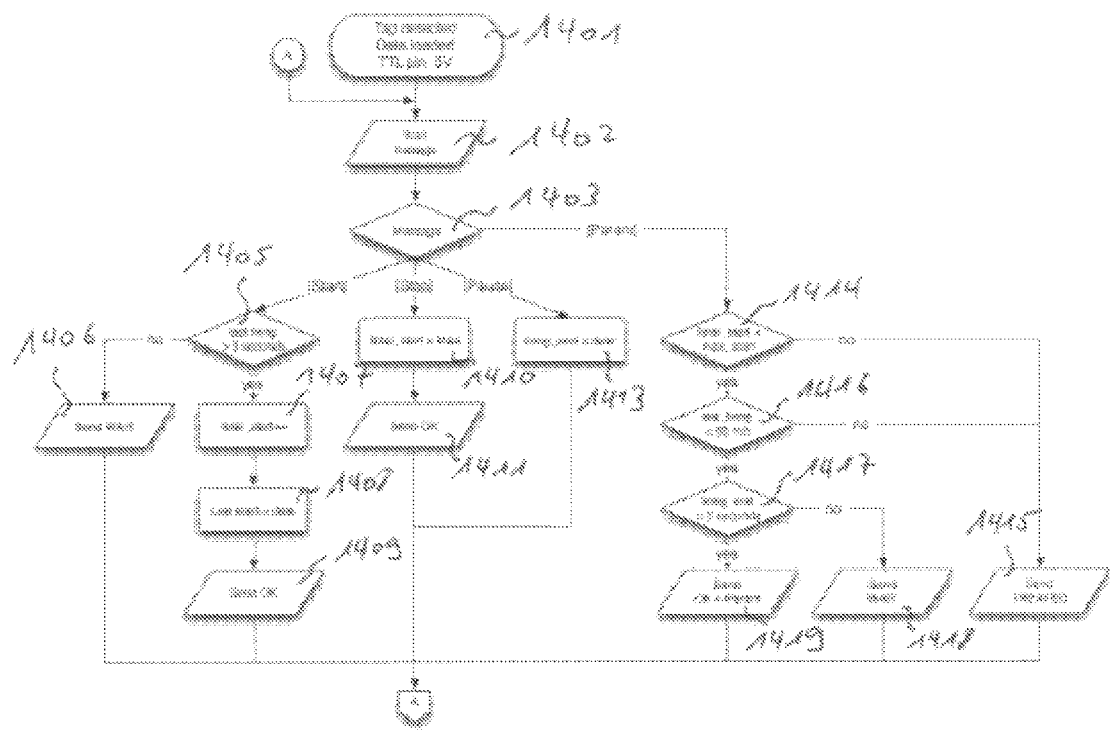

FIGS. 13 and 14 are logic flowcharts showing the processes at work in the microcontrollers in a device as claimed in the invention.

Figure 15:
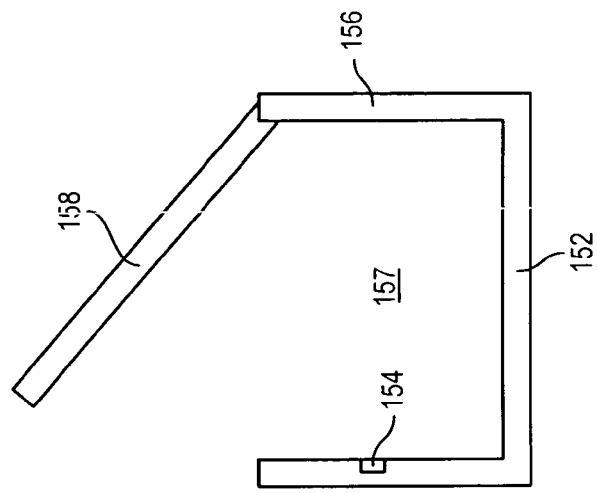
Figure 15:
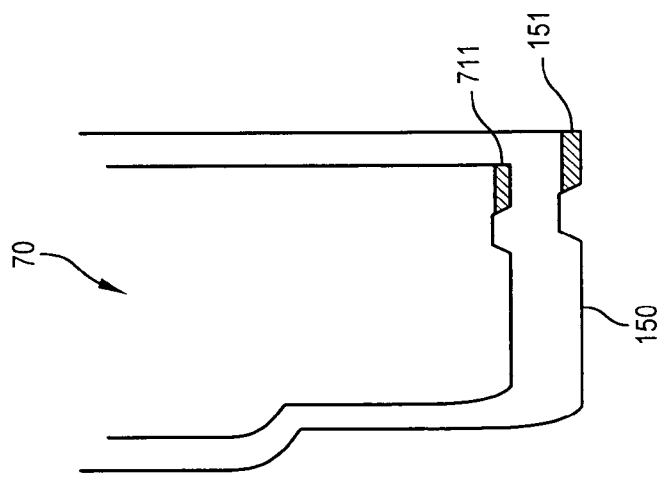

FIG. 15 represents a device and a sleeve as claimed in a particular embodiment of the invention.

Figure 16:
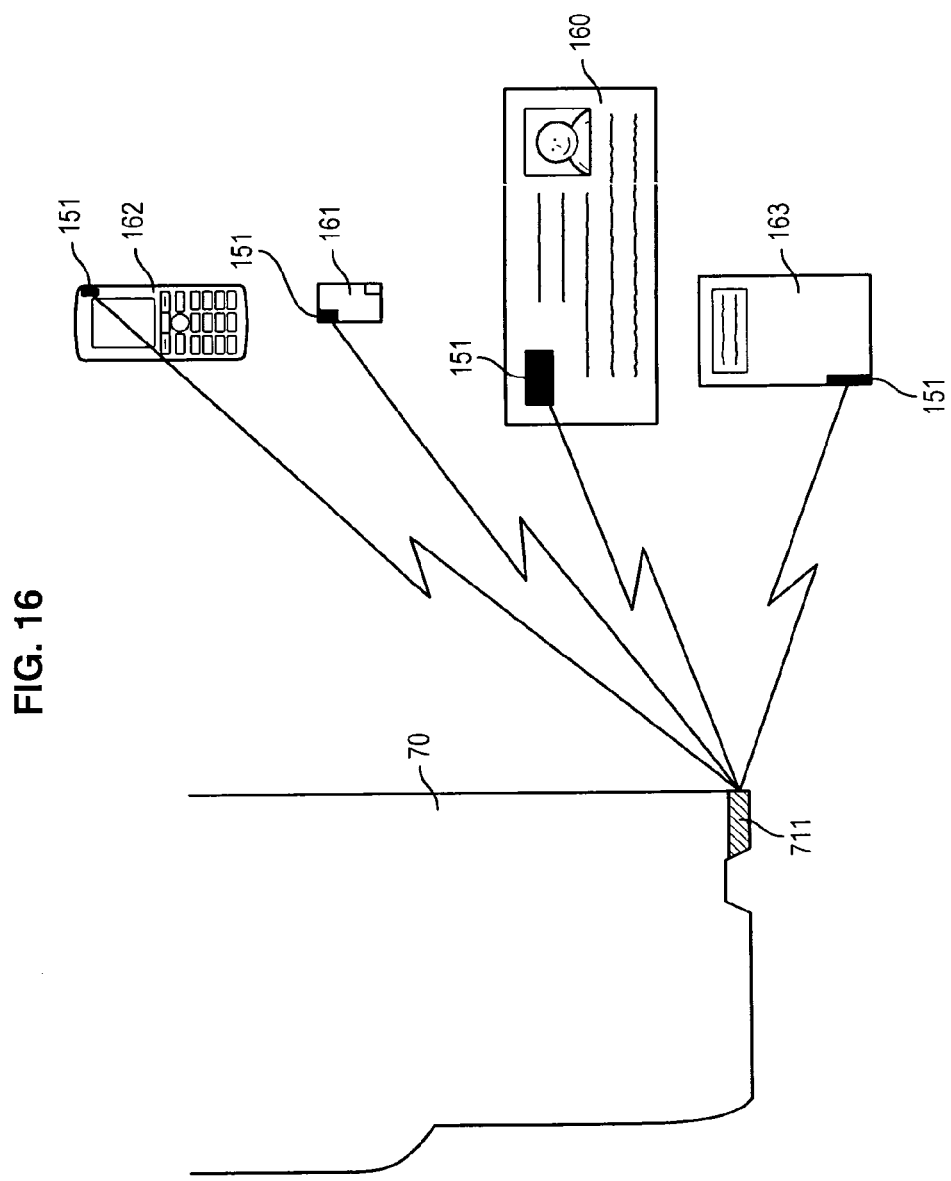

FIG. 16 represents a device and portable elements as claimed in a particular embodiment of the invention.

The invention is based on moderate heating to provide heat treatment to a limited volume of cutaneous tissue surrounding and including a present or future cutaneous lesion (a future lesion, for instance, in the case of surgical incisions). As stated above, it is not a matter of selectively heating one or more skin constituents, but effectively heating the whole of an area located throughout the thickness of the skin (epidermis, dermis, upper layer of the subcutaneous tissue) to generate a biological response to the heat stress or thermal conditioning throughout the tissue. The choice of beam and all related parameters is therefore based on these specifications.

Figure 1:
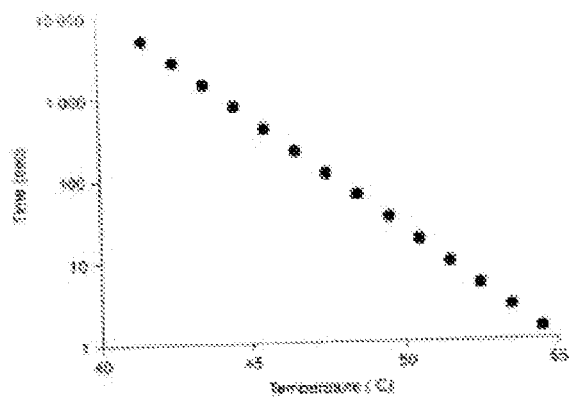
FIG. 1 is a graph illustrating a logarithmic relationship between exposure time and temperature for inducing a heat shock response.

FIG. 1 illustrates a logarithmic relationship between exposure time on the y-axis (units in seconds) and the temperature for inducing a heat shock response along the x-axis (units in degrees Celsius). Heat shock response is a cellular mechanism used to maintain stability when a shock (e.g. heat shock) is undergone. The heat shock response often involves the production of heat shock proteins (HSP), a protein group that can help accelerate the healing process.

The invention does not aim to alter the cell structure, but to influence the healing process by inducing HSP production. Indeed, uncontrolled hyperthermia can quickly lead to tissue damage and consequently to tissue denaturing and destruction. Using thermal conditioning, the invention provides for induction of a localised fever, the maximum temperature of which is controlled to avoid the appearance of tissue damage.

By directing a source of electromagnetic energy such as a laser at the wounded tissue zone, thermal conditioning is induced such as to alter the inflammatory process. The link between a controlled temperature increase (moderate hyperthermia), HSP production and the inflammation process has already been established in the prior art.

Figure 2:
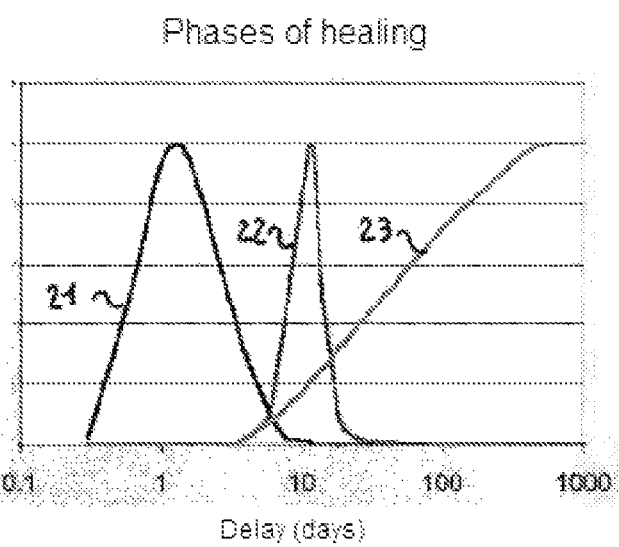
FIG. 2 is a graph illustrating the different phases of healing of a cutaneous wound.

As shown in FIG. 2, the healing process can be broken down into three phases following the initial thrombosis:
  inflammation (21),
  proliferation (22) and,
  remodelling (23).

The x-axis of this graph shows the time since the start of healing and the y-axis shows a given heat shock response level and hence a level of HSP production.

The process of treating a patient's skin wounds using a laser beam consists of directing light energy onto the tissue with the aim of generating moderate and controlled hyperthermia as early as possible in the healing process in order to prevent scarring and accelerate tissue regeneration, rather than correcting this scarring once the scar itself has appeared. The time at which the wound is treated must therefore be selected carefully with respect to the inflammation phase.

An optimum treatment window should be defined, to ensure that the peak of HSP production coincides with the inflammation phase. Since the HSP production peak may occur up to 24 hours after heat stress has been undergone, the conditioning treatment may take place up to 24 hours before the lesion appears.

Beam Selection:

The choice of beam and all related parameters is based on precise specifications. A digital simulation model was used, based on the finite element method, taking into account interactions between the light and the main chromophores in the treatment region, in order to confirm the theoretical choices.

Figure 3:
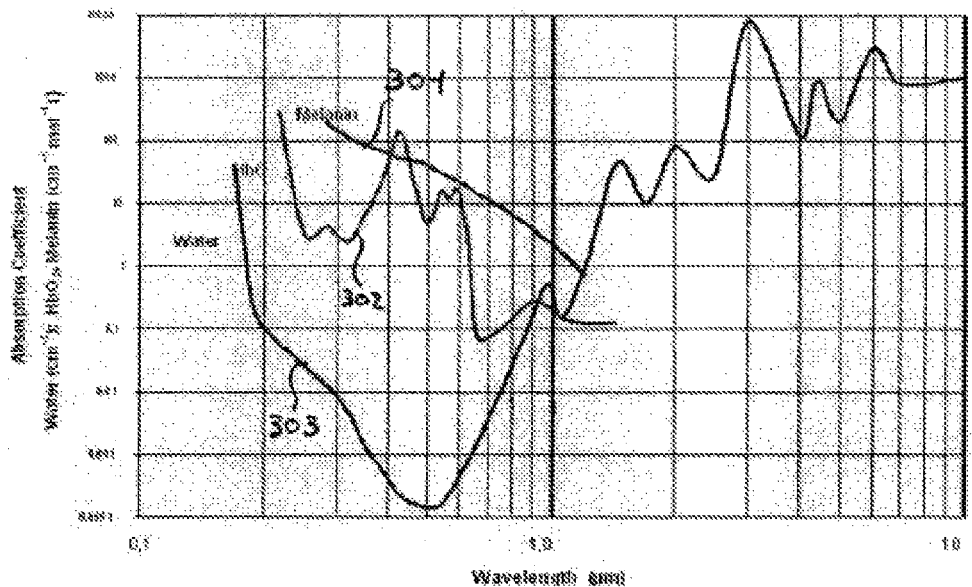
FIG. 3 is a graph illustrating the different absorption coefficients of the main chromophores as a function of the wavelengths of the laser source emitted.

Wavelength Selection:

FIG. 3 is a graph with three curves showing the energy absorption coefficient (y-axis) as a function of the energy wavelength (x-axis) for the following skin constituents:
melanin, shown as curve 301,
haemoglobin, shown as curve 302,
water, shown as curve 303.

Figure 4:
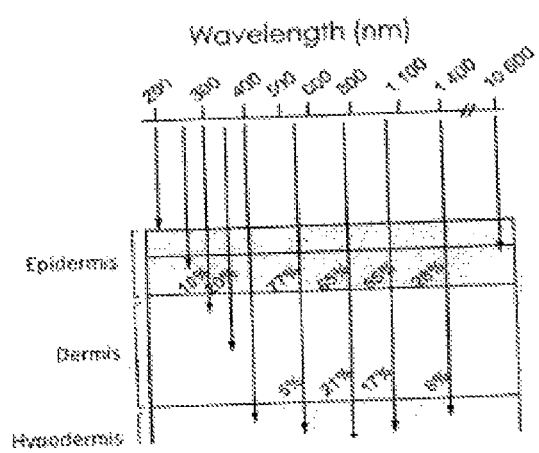
FIG. 4 is a graph illustrating the skin penetration (as a percentage) of a laser beam as a function of its wavelength.

FIG. 4 is a graph showing the rate of absorption of each skin layer for each wavelength.

Referring to these figures, we can see that light absorption by the various chromophores can vary considerably according to the wavelength.

Since the melanocytes are located in the basal layer of the epidermis, the wavelength must be greater than 800 nm in order to pass through this layer without being fully absorbed. At wavelengths of less than 590 nm, haemoglobin is the predominant chromophore and is therefore highly absorbent. However, at red and near-infrared wavelengths (between 600 nm and 1000 nm), there is relatively little absorption since neither water nor blood absorb energy at these wavelengths. Finally, for wavelengths greater than 1800 nm, absorption of water is extremely high and this absorption becomes the predominant factor.

The range of wavelengths to be used must therefore be between 800 nm and 1800 nm. In a preferred embodiment, the wavelength will be 810 nm or 910 nm. Advantageously, wavelengths of 1,200 nm would minimise absorption by melanin, but current technology does not provide a sufficiently powerful beam from a laser diode source at this wavelength.

Spot Shape Selection:

The shape of the laser spot must also be designed in order to provide deep heating and stimulate all tissues involved in the skin wound healing process: the hypodermis, dermis, and epidermis. Since depth is near-proportional to the laser spot diameter, a diameter greater than or equal to 3 mm will be preferred in the case of a round spot. Ideally, the spot shape could also be tailored to the geometry of the area to be treated, to enable the most homogeneous distribution possible of light energy within the target tissue. In a preferred embodiment, a rectangular spot shape whose width is at least 3 mm and whose length may be several centimeters could be used to treat linear wounds.

Temperature Precision in the Heated Volume and Laser Beam Profile:

The invention additionally relates to the temperature precision achieved within the heated volume. The digital model developed can be used to optimise all parameters and achieve a minimum temperature of 45° C. (temperature required to induce heat stress) and a maximum temperature of 55° C. As described in the prior art, temperatures in excess of 60° C. can induce protein denaturing and therefore counteract the desired effect. The maximum temperature of 55° C. means that this threshold value will not be exceeded.

Figure 5:
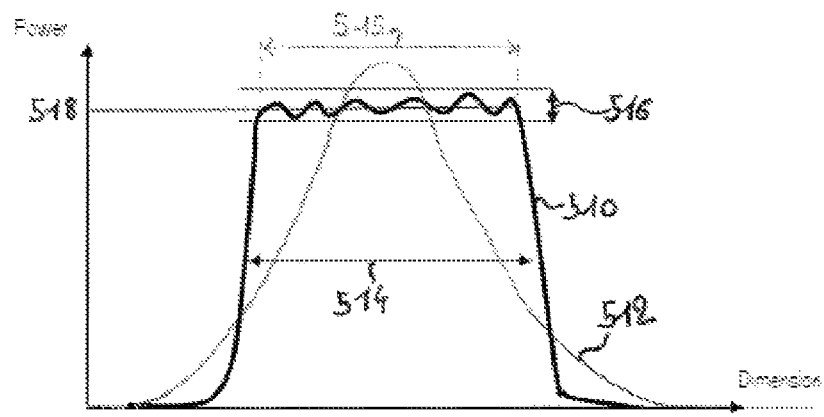
FIG. 5 is a graph illustrating a conventional laser beam profile and a laser beam profile as claimed in the invention.

For these reasons, and as shown in FIG. 5, which illustrates both a conventional Gaussian beam profile (curve 512) and the beam profile of a device as claimed in a possible embodiment of the invention (curve 510), a conventional Gaussian beam profile is not the most suitable profile. Indeed, as the name suggests, the energy distribution is similar to a Gaussian function, which has the direct effect of heating the skin surface in a non-uniform manner, with a major temperature peak in the centre of the irradiated zone. The temperature gradient will therefore be too great as compared with the precision of the temperature range in which it is desirable to operate.

A flat-top (or top-hat) profile (510) is consequently to be preferred to a Gaussian profile in order to ensure the skin surface temperature is homogenised, and therefore the temperature in the volume heated.

This flat-top power profile, shown as curve 510, gives a more homogeneous heating effect throughout the heated area, rather than a selective heating action. This profile is defined by two components:
the ratio of wavefront width (515) to full-width half-maximum (FWHM) (514).
the rate of variation (516) along the wavefront width (515).
and nominal power (518) which is the mean power along the wavefront width (515).

One feature of a flat-top profile is a minimal rate of variation (516) along the wavefront width, with a maximal wavefront width-to-FWHM ratio. Advantageously, a flat-top profile will have a rate of variation of less than 5% and a ratio of wavefront width-to-FWHM of greater than 90%.

The spot shape will depend on the medical indication. In a preferred embodiment and in a configuration chosen for treating incisions, the spot dimensions will be 20 mm by 4 mm, and the rate of variation less than +/−20% of nominal power (518).

In order to achieve this particular profile, the invention provides a means for shaping the laser beam emitted by the diode (since the laser beam has a Gaussian profile on output from the diode). The system in question is shown in FIG. 6.

In one possible embodiment of the invention therefore, the means of shaping the laser beam (61) is positioned downstream of a laser diode (62), advantageously characterised in that its emission width is 200 µm by 5 µm and its divergence is 8×35°. An optical fibre (63) positioned in front of the diode acts as a cylindrical lens to reduce divergence of the diode's fast axis advantageously to approximately 5°. The laser beam then passes through the laser beam shaper (61), which comprises a system of two lens arrays (64) and a cylindrical lens (66), which splits the original beam into as many beams as there are lenses in the lens array (64). Each sub-beam is focused at the desired distance and all these beams are then superimposed to achieve a flat-top profile.

The beam's focal distance depends chiefly on the focal length of the cylindrical lens. The homogeneous nature of the profile depends however both on the focal length of the cylindrical lens and on the focal lengths of the two lens arrays. Furthermore, to achieve the most homogeneous flat-top beam possible, the input beam must strike as many lenses in the array as possible (the greater the number of sub-beams formed, the more the sub-beams tend to a flat-top profile when combined). There is, therefore, a balance to be struck between the distance between the diode and the first lens array and the angle of divergence, in order to maximise the homogeneity of the flat-top profile, whilst reducing the length of the final system.

PREFERRED EMBODIMENTS

In order to make the technique as accessible to as many users as possible, the device is designed to be easy and safe to use under all circumstances and in all locations in which it may be used, from a general practitioner's surgery to the sterile environment of an operating theatre. Since users of the device may need to travel or make regular visits, the size and portability of the device is also a key factor. In addition, as described above, the invention provides for the light source to be applied as early as possible in the healing process in order to prevent the appearance of scarring, rather than correcting this once the scar has appeared. For this purpose, users need a medical device that can enable early intervention, i.e. directly in the operating theatre in a sterile environment.

The medical device should therefore be designed to be small, portable, easy to use with one hand and autonomous (wireless) and further designed to avoid jeopardising the cleanliness or sterility of the environment in which it is used.

One embodiment of a device as claimed in the invention will now be described, referring to FIGS. 7 and 8.

A dermatological treatment device (70) as claimed in the invention, which comprises a closed optical unit (722), including at least one laser system (72) comprising a power laser diode whose wavelength is between 750 nm and 1400 nm and whose power is greater than 1 W and less than 25 W, and a conversion means (74) consisting of a lens array or a phase array. The laser system (72) and conversion means (74) are designed to emit a laser beam with the aforementioned advantageous characteristics. The optical unit (722) may also include a sighting laser (73), whose power is less than 1 mW for instance, in order for said sighting laser to provide comfort in use and not generate any biological response. In order to ensure this sighting laser (73) is visible, its wavelength may for instance be between 480 nm and 650 nm (red colour).

The invention provides for the optical unit (722) to be removable and interchangeable in order to facilitate maintenance of the treatment device (70) and ensure its flexibility (ability to change diode type according to the desired treatment type). The invention therefore provides the device user (e.g. medical practitioner) with a panel of optical units, each of which will have different configurations while at the same time complying with safety-related constraints (the user cannot change the settings him/herself).

The treatment device (70) also comprises a battery element (71) so that the device can be fully independent from the point of view of its energy supply. This battery may be interchangeable.

The treatment device (70) includes one or more electronic circuits (710) whose function is to manage the general power supply to the device and to the various components included in the device.

The treatment device includes an RFID reader (711) (e.g. RFID antenna), used to make the device safe by ensuring that the laser only fires when it is in the vicinity of an RFID component (tag) affixed close to the treatment area, thus preventing any risk of harm for the user, patient and other nearby persons. This system also enhances treatment safety by reading pre-recorded settings from the tag, meaning that the practitioner cannot accidentally change any parameter that is potentially dangerous to the patient (chiefly laser power and firing time). The laser firing settings are controlled on the basis of information transmitted by the RFID component, which contains parameters that can be used to adjust the firing power, firing time and number of pulses, according to the user's choices.

The user will select the component according to the nature of the treatment to be performed, and the tag selected will transmit a signal or information to the receiver which will control the laser emissions. The component consists for instance of a patch formed by a piece of adhesive fabric that includes a radio frequency identification (RFID) tag, consisting of an antenna design that enables inductive coupling for powering a high frequency component and transmission of a high frequency signal emitted by this component.

The component must be placed close to the treatment zone such that the treatment device (70) is within interaction range of the tag throughout the duration of treatment.

These RFID components are widely described in the prior art. However, the invention envisages that the RFID component also plays a role in automating the process. In fact, the RFID component has an identifier which refers to a settings table in the laser software. This table contains preset values for firing power and firing time and also the type of patient to be treated (for a safety check by the practitioner). When using the device, the user simply selects the safety strip (containing the RFID components) based on the patient's skin phototype and indication (wound, acne treatment, skin remodelling etc.). Unlike other laser systems on the market, the user cannot adjust the operating settings. Treatment parameters are therefore based solely on the choice of strip containing the treatment identifier.

Advantageously, the distance between the RFID component and the treatment device (70) is between one and fifteen centimeters. This distance is assessed by the limited range of the means of interaction between the component and treatment device (70) or by a range-finder, for instance an ultrasound range-finder integrated into the device.

The treatment device also includes a pyrometer (712), used to monitor the temperature increase that can cause superficial burning (temperature greater than 60° C.). The pyrometer (712) is used to set up a closed loop on the laser beam. The pyrometer (712) is in fact a safety component that monitors skin surface temperature. It operates to "lock down" or deactivate laser firing if the temperature reaches a preset threshold value. The pyrometer (712) can also be used in a more advanced way within a closed control loop in order to readjust the laser settings.

In general, the temperature at the surface and deeper in the epidermis will depend on a variety of parameters such as:

1—wavelength, which is a key factor in the absorption and scattering of light by the various chromophores (water, haemoglobin, melanin).

2—laser power, causing heating to a greater or lesser depth.

3—spot shape and size, which influences the heat distribution at depth.

4—beam profile, which has a direct input on the temperature gradient across a beam cross-section (Gaussian profile, flat-top profile).

5—firing time which, associated with a given power, if it is long promotes a heat diffusion heating system.

6—finally, parameters directly related to the patient, the most significant of which is likely to be the skin phototype.

There may not therefore be a general correlation between the surface temperature of the epidermis and the temperature of lower layers. On the other hand, if all laser-related parameters (points 1 to 5) are fixed, it is possible to "predict" the temperature increase in the tissue on the basis of a human factor, and therefore from the phototype.

In addition there is provision for a transparent optical window (713) in the wavelength range between 480 nm and 1.4 µm. In a preferred embodiment, potassium bromide that is transparent to wavelengths from 450 nm to 10 µm could be chosen.

A standby system could be also added to the device, to operate when the device is not used for a preset length of time. Standby mode is interrupted as soon as the user presses either of the firing buttons. This type of system saves battery power, on the one hand, but in particular prevents the sighting laser (even a low power laser) from causing eye damage.

In addition, the treatment device could include a cooling system comprising an internal radiator (714) connected directly or via a heat pipe to the laser diode. Furthermore, one possible embodiment of the invention provides for a natural and/or forced ventilation device to evacuate heat generated by the laser diode from the device in a sterile manner in order to avoid jeopardising the sterility of the operating area above which the treatment device (70) is used.

Advantageously, the device could be fitted with a user interface to provide the user with information on the operating parameters (wavelength, settings contained in the RFID component and read by the RFID treatment device, temperature measured by the pyrometer).

We will give details of a treatment device's user interface as claimed in the invention. Advantageously, the treatment device's user interface as claimed in the invention includes the following items:

- an LCD screen (75), used for feeding back information to the user on device operating settings and parameters (the LCD screen may be a touch-screen).
- an emergency stop button (76), which the user can activate to stop the device quickly in a emergency.
- an on/off button (77) to switch the device on or off.
- a double button system (88) to trigger and secure the laser: the double button system (two buttons, one on either side) makes the firing operation safe in that the laser can only fire when both buttons are held down by the user. As soon as the user releases either button, the laser immediately stops firing. Consequently, if the handpiece were to be inopportunely placed on a work surface and one of the buttons was resting on an item on the work surface, the laser could not fire.
- an indicator light (89) to show the user that the device is operating,
- a buzzer (717) to warn the user of a problem (battery problem, too high temperature measured by the pyrometer).

Advantageously, a possible embodiment of the invention provides for a removable sterile sleeve (80) designed to contain the device and isolate it from the outside surroundings. This sleeve can be understood as a sterile casing in which the device is placed in order to ensure that the area in which the device is used remains sterile. Advantageously, the removable sleeve (80) is designed not to interfere with the laser beam. For this purpose the device is provided with a window that is transparent to the preset wavelengths, in order to allow a beam whose wavelength is within the range of preset wavelengths to pass through. The removable sleeve (80) is also designed not to interfere with the operation of the pyrometer (712). The removable sleeve (80) also allows heat removal without having a detrimental effect on the sterile environment in which the treatment device (70) is used. Using this sleeve, the laser can be fired without altering the sterility of the sleeve's outside surfaces.

The sleeve must obviously be sealed and have a sealed closure system, so as to create a microbial barrier between the device and its surroundings. Nevertheless, this sterile barrier must not hinder the removal of heat generated by the device. The sleeve therefore contains at least one air filter and preferably at least two air filters (an air inlet and air outlet filter) to allow air circulation inside the sleeve.

Moreover, the sleeve must not hinder access to the device controls (firing buttons, switch, emergency stop button), it must not prevent information from being read (LCD screen, indicator lights) or the device from being gripped. In a preferred embodiment, the sleeve should therefore comprise a rigid section at the bottom of the device for correct positioning and a flexible transparent upper section covering the rest of the device.

Since surfaces 81 and 82 of the sleeve are in contact with the patient particularly when treating an incision, the risk that the sleeve could come into contact with blood should not be ignored. In fact, if the sleeve is in contact with blood, blood may accumulate on it as it is moved across the rest of the incision; the laser beam passing through the sleeve could be absorbed by these traces and consequently lose part of the treatment energy in this zone. In a preferred embodiment, the treatment device (70) and the lower rigid part (87) of the sleeve (80) in contact with the treatment area both include a recess (83) opposite the laser beam output, ensuring there is no direct contact with the patient and therefore no fouling or contamination and ensuring a distance between the beam shaper output and the tissue zone to be treated.

The sleeve therefore comprises one rigid section and one flexible section (for operation of the buttons and ease of holding). It is intended that both sections should be made of PVC, with a thickness for example of between 2 and 3 tenths of a millimeter for the flexible section and a few millimeters for the rigid section.

RFID Component

As shown in FIG. 9, and as described above, treatment is made safe and controlled by means of a safety strip (90) containing an RFID chip which transmits the various operating settings to the laser device, on the basis of the medical indication and skin phototype of the patient to be treated. This safety strip (90), which may be produced in several different lengths (e.g. 4, 10 and 20 cm), is affixed approximately 5 mm away from the zone to be treated.

The safety strip comprises two adhesive elements: one double-sided adhesive element (91) and another single-sided adhesive element (93). These two elements sandwich the RFID components (92), which are arranged every 2 cm. The safety strip may, for instance, be 2 cm wide.

The lower adhesive element (91) is in contact with the patient's skin. It must therefore be biocompatible and offer appropriate adhesion to the skin during use. The lower adhesive element (91) must stick to the patient's skin and also bond with both the RFID component and the upper adhesive element (93). The lower adhesive element is therefore a double-sided adhesive.

A sterilisation stage is included in the manufacturing process used to produce the safety strips.

The upper adhesive element (93) must be a single-sided adhesive element in order to permit assembly with the RFID component (92) and lower adhesive element (91). As shown in FIG. 10, there is provision for printing information on the upper section (93), such as the skin phototype, the company name, a scale to help the practitioner gauge progress of the treatment, along with the product reference.

The upper adhesive element (93) is designed not to interfere with RFID communication between the device's RFID reader (711) (see FIG. 7) and the RFID components (92).

The RFID components must comply with ISO standard 15693-3. There is also provision for the mandatory and optional sections, as defined by this standard, to be implemented as well. Since RFID transmission range is critical, the RFID components (92) as claimed in the invention are such that this value can be set once the "RFID component—RFID reader" pair has been selected. The size of these RFID components may for instance be 14 mm×14 mm and their thickness less than 1 mm. The EEPROM storage capacity of the RFID component shall be at least 1024 bytes. In addition there is provision for a sterilisation process using ethylene oxide.

Communication Process Between the RFID Component and the Device

As shown in FIG. 11, the device is composed of two microcontrollers (111 and 112). One (microcontroller 111) is responsible for managing the laser, the energy, the heat control and the UI; the other (microcontroller 112) for managing the safety strips (90). As for management of firing, this is shared by the two controllers (111 and 112). Firing may be stopped due to a too high temperature (managed by microcontroller 111) or due to activation of the emergency stop (microcontroller 111). Resumption of treatment is constrained by these two conditions that cause the device to stop.

Referring to FIGS. 12a, 12b and 12c, the pyrometer (712) (see FIG. 7) stops the laser if the skin temperature exceeds a critical temperature, for instance 60° C. (managed by microcontroller 111). These figures are graphs which show temperature curves 120, 121 and 122 (temperature in degrees Celsius on the Y-axis) as a function of heating time TC (on the X-axis); TC1, TC2 and TC3 represent the time at which laser firing is stopped. If the laser has been stopped by the pyrometer (712), firing can be authorised once more a single time only, after a safety delay (e.g. 5 seconds) if during the first laser emission, the firing time was less than or equal to half the preset firing time (as managed by microcontroller 112). This is the case in FIG. 12c. The figures therefore illustrate the following scenarios:

FIG. 12a illustrates a scenario in which the laser is stopped (TC1) after 50% of the preset firing time has elapsed; in this case the laser treatment cannot be resumed.

FIG. 12b illustrates a scenario in which the laser is not stopped before the end of the preset firing time (TC2).

FIG. 12c illustrates a scenario in which the laser is stopped (TC3) before 50% of the preset firing time has elapsed; in this case the laser treatment may be resumed.

If the pyrometer (712) trips after 50% or more of the normal firing time has elapsed (FIG. 12a), the end of normal firing should be indicated with a beep (microcontroller 111). If the pyrometer (712) trips before 50% of the time has elapsed, a display on the user interface will indicate to the user that laser treatment may be resumed.

If the user stops the laser voluntarily or otherwise and the elapsed time is less than or equal to 75% of the preset firing time, the laser treatment may be allowed to resume once, after a 5 second delay. This re-authorisation is valid for a 60 minute period.

If the emergency stop system trips (FIG. 7, button 76), a checking procedure could be provided.

The presence of an RFID component (92) is indicated by the TTL pin (113) on the microcontroller (112). The presence of an RFID component (92) gives no information regarding its status. To find out the status of the RFID component (92), a "read settings" message must be sent to the microcontroller (112). This command lets you find out information on the treatment status of the RFID component (92) which is in the range of the RFID reader (711). The status of an RFID component (92) may be one of the following:

Treated.
OK (Not Treated).
Immediate resumption (identical to not treated).
Wait then resume (5 seconds).

Microcontroller 111 Recognises Five Messages from Microcontroller 112:

INIT: Initialisation of the clock and device identification.
PARAM: Retrieve information on RFID component (92) status, firing power and firing time (firing only allowed if status is OK).
START: Start of firing.
STOP: End of firing.
PAUSE: Stop firing prematurely.

When the device starts, microcontroller 111 initialises the clock in microcontroller 112 with the INIT message. Both clocks are synchronised. At the pulse edge of the TTL pin (113) of microcontroller 112, microcontroller 111 requests the firing settings via the PARAM message. Depending on the response from microcontroller 112 the user interface is updated and firing is authorised. During firing, microcontroller 111 indicates firing progress to microcontroller 112 with the messages START, STOP and PAUSE. Microcontroller 112 updates RFID component (92) information according to these messages. The device's clock is managed by the microcontroller 111. It does not contain the exact date and time, but timing information relating to the device start-up. It operates as a timer. The device clock may be reinitialised following extended battery power loss. In this case, if an RFID component (92) has been treated, its treatment start date is later than the current date. Even if treatment is not finished, the RFID component (92) is considered as treated.

FIG. 13 illustrates a logic flowchart for microcontroller 111. Thus box 1301 shows detection of the presence or otherwise of an RIFD component; if not detected, the user interface indicates that no RFID component was found (box 1302). If an RFID component is detected, the parameters are read (box 1303) in order to diagnose RFID component status (box 1304). If the status is OK, the device indicates via its user interface that it is "ready" (box 1305), and if the firing button is activated (box 1306), then microcontroller 111 sends microcontroller 112 the START message (box 1307) to indicate that laser emission should be started. Finally, the laser is switched on (box 1308). If the message is WAIT, the device indicates that it is on "standby" (box 1309) and returns to the start of the flowchart. If the message is TRT OK (treated), the device indicates that the zone has been treated (box 1310) and returns to the start of the flowchart.

If firing is initiated (box A), temperature measurement (box 1311) is performed. If this temperature is greater than 60° C., a time measurement (box 1312) is also performed. If this time value is less than 50% of the preset firing time, a PAUSE message (box 1313) is sent to microcontroller 112 and the laser is switched off (box 1314).

If the temperature measured in 1311 is less than 60° C., a time measurement (box 1315) is also performed. If this time value is less than 75% of the preset firing time, a further temperature measurement (box 1311) is performed. If, on the other hand, the time value is greater than 75% of the preset firing time TC, a STOP message (box 1316) is sent to microcontroller 112. A temperature measurement is then performed (box 1317), and if the temperature is less than 60° C., the firing time is checked (box 1318); if the actual firing time is less than the preset firing time TC (meaning that the laser treatment has not yet finished), a further temperature check is performed (back to box 1317). This loop continues until the temperature exceeds 60° C. or the firing time reaches or exceeds TC. In either case, the laser is turned off (box 1320), a beep is sounded (box 1321) (or any other user interface signal) to advise the user that treatment of this zone has finished, and an end of treatment message is displayed (box 1322). Coming back to box 1312, if the actual firing time is greater than 50% of TC, a STOP message is sent to the microcontroller (box 1319) and the laser is turned off (box 1320). If the actual firing time is less than or equal to 50% of TC, a STOP message is sent to the microcontroller (box 1319) and the laser is turned off.

As shown in FIG. 14, a firing authorisation management logic flowchart for microcontroller 112 will now be described. If an RFID tag is detected (box 1401), microcontroller 111 waits for a message (box 1402). When a message (box 1403) is received, it is analysed. If the message is START, and the laser was last fired less than 5 seconds ago (box 1405), microcontroller 111 sends the WAIT message (box 1406). If, on the other hand, the laser was last fired more than 5 seconds ago, the total_start variable (indicating the number of times the laser has fired) is increased by one increment (box 1407) and the last_start variable (indicating the time at which the laser last fired) is updated (box 1408). Finally an OK message is sent (box 1409).

If the message received is STOP, the total_start variable is set to a predetermined maximum (box 1410) and the OK message is sent (box 1411).

If the message received is PAUSE, the end of firing time is recorded (box 1413).

Finally, if the message received is PARAM, the total_start variable (box 1414) is analysed. If this variable is lower than the specified maximum, the TREATED message is sent (box 1415). If not, the last_start variable (box 1416) is analysed. If this variable is lower/greater than 60 minutes, the TREATED message is sent (box 1415). If not, a check is performed to see whether the laser was last fired more than 5 seconds ago (box 1417). If this is not the case, the WAIT message is sent (box 1418). If, on the other hand, the laser was last fired more than 5 seconds ago, the OK message is sent and the settings are read (box 1419). The information in the RFID component may be selected from the following options: unique RFID component identifier, manufacturing date, expiry date, device settings identifier based on skin type and the safety strip manufacturing batch number.

Obviously, all the numerical values in this description (e.g. percentages, temperature etc.) are given simply for reference in order to guide production of the invention. Other numerical values could therefore be used for instance as determined by experimentation, whilst still remaining within the scope of the invention.

In a possible embodiment of the invention, there is provision for the adhesive attachment element to have a threefold safety role:
  making the device safe by immediately stopping the device from operating when the RFID component (92) in the adhesive attachment element (90) is no longer within range of the RFID reader (711) in the device.
  defining the treatment settings. The user selects the adhesive attachment element according to the indication and patient's skin type, and the pre-programmed RFID components (92) within the adhesive attachment element (90) directly transmit the appropriate parameters to the device.
  protecting integrity (single use). When in use, the device records information about treatment status on the RFID components (92) in the adhesive attachment element. Treatment status may be as follows: zone to be treated has not been treated, zone to be treated is being treated, and treatment of the zone to be treated has finished. Once treatment is completed, the device, upon receiving information about the status of the zone to be treated, has a means of preventing reuse of the adhesive attachment element (90) provided with a means of identification when this has already been used once for treating a treatment zone. This RFID component locking principle ensures that each adhesive attachment element can only be used once. The direct benefit of this system is that it prevents:
    a second treatment in the same place (elimination of the risk of overdose).
    reuse of a used adhesive attachment element which was sterile when delivered.

There is provision for the means of preventing reuse of the adhesive attachment element (90) to be included in the RFID component itself directly.

Scenarios of Surfaces to be Treated

In certain medical or dermatological applications, treatment must be applied to surfaces and not to "linear" zones as is the case with an incision for example.

The device must therefore be moved over the whole surface to be treated, something that makes it difficult or impossible to attach a safety strip along the zone to be treated as described previously. In fact, when the zone to be treated is "linear", the strip may be easily fixed beside and along this zone to be treated. This is not the case when the treatment zone is a surface. There are also other reasons why such a safety strip cannot be applied beside the treatment zone: for example depending on the position of the treatment zone on the body, applying such a safety strip may be difficult (joints, locations) or depending on the nature of the skin in the area to be treated, applying such a strip may present specific problems (allergy, applying to the mucosa, etc.).

As shown in FIG. 15, and in order to resolve any difficulties linked to the application of a safety strip, there is the option of providing the safety sleeve (150) (identical to sterilisation sleeve 80) with an RFID component (151) the same as the one described within the safety strip, that is to say the sterilisation sleeve (150) could comprise an RFID component, itself comprising storage space intended in particular for recording information regarding firing and/or firing authorisation parameters as described previously.

The practitioner therefore chooses the sleeve according to the patient to be treated and/or the type of treatment to be given. When the sleeve is positioned correctly on the treatment device, the device's RFID reader reads the information and firing parameters contained in the sleeve's RFID component. Thus the device operates in combination with the sleeve (and more specifically with the sleeve's RFID component). This sleeve/treatment device treatment unit is improved by the interaction between the sleeve's RFID component and the device's RFID reader. Such a sleeve/treatment device combination ensures that the device is used properly with a sleeve and therefore ensures sterilisation during treatment: in fact if the device is used without the sleeve no firing parameters or firing authorisation are given.

The energy source's operating parameters are memorised in the sleeve's RFID component and are communicated to the device for controlling the energy source (the laser for example). Preferably the RFID component operates in the frequency band of between 13 and 14 MHz.

However, in a situation where the zone to be treated is a surface, treatment is generally longer than when the area is "linear". Thus a particular embodiment of the invention stops the sleeve's RFID component from preventing reuse and authorises as many laser firings as necessary for treating the surface.

As shown in FIG. 16, the RFID component (151) can also be included in another object such as the practitioner's identity card (160) or any other portable item (name tag (161), telephone (162), bleeper (163) . . . ).

Thus a practitioner wishing to use the device (70) must acquire this portable object (160, 161, 162 or 163) comprising the RFID element (151) in order to be able to use the treatment device (70). In this way, the device's (70) reader (711), in communication with the portable element's RFID component (151), is able to read information regarding operating parameters and/or firing authorisations. Such an embodiment of the invention means that only the person wearing this portable object comprising the RFID element would be able to use the treatment device (70).

Sterilising the Sleeve

As the sleeve is the part of the device in contact with the patient's skin and more generally with the patient's environment, a process for sterilising the sleeve is essential and indispensable so that the sleeve cannot be used without it first being sterilised.

As shown in FIG. 15, the sleeve's (150) RFID component (151) includes storage areas intended in particular for recording information regarding sterilisation of the sleeve. This information is characterised by the sleeve's sterilisation status. At the same time there is provision for a steriliser (152) intended for sterilising the sleeve (150) to contain an RFID component (154) able to read and write to the storage space in the aforementioned RFID component (151) included in the sleeve (150). It should be remembered that a medical steriliser is a medical instrument used for sterilising medical tools and accessories. Depending on its principle of operation, the steriliser comprises a tube that causes warming within the steriliser. This tube emits ultra-violet radiation; these rays strike the internal walls of the steriliser. The ultraviolet rays are transformed into ozone and sterilise the tools; these rays have a powerful germicide effect. Operation of the steriliser is in particular ensured by a door (158) (combined with walls (156)) suitable for ensuring that the steriliser's (152) enclosure (157) is hermetically sealed.

A process for sterilising the sleeve (150) comprises the following stages therefore:

Place the sleeve (150) in the steriliser's (152) enclosure (157).

Close the hermetically sealed door (158).

Read the information contained in the RFID component (151) of the sleeve (150) to find out whether the sleeve is sterile or not (in which case the user of the steriliser can be warned that the sleeve has already been sterilised; the sterilisation process can also be started).

Start the sterilisation process.

At the end of the sterilisation process, using the RFID component (154), change the information written to the storage area according to which the sleeve has been sterilised as well as the date of sterilisation.

A process for using the sleeve (150) comprises the following stages therefore:

Place the treatment device as claimed in the invention in the sterilisation sleeve.

The RFID reader (711) belonging to the device as claimed in the invention queries the sleeve's RFID component to find out whether or not the sleeve has been sterilised and the date it was last sterilised.

Decide on the basis of this information whether the sleeve can be used or not. The relative question is to know whether the sleeve may be considered as sterile or not; firing authorisation for the device depends on this decision.

If the sleeve should not be used (sleeve not sterile), activate a visual and/or audible alarm in order to alert the user to the fact that the sleeve must not be used. The device is also designed such that in these circumstances firing is not authorised. If the sleeve is considered as sterile then firing is authorised.

The decision according to which the sleeve is sterile or not is not taken based on information collected from the sleeve's (150) RFID chip (151). If this information shows that the sleeve is not sterile or that it was last sterilised before a certain specified date (for example 24 hours), then sterilisation is no longer guaranteed and the decision is taken that the treatment device may be used.

On the other hand, if according to this information, the sleeve has been sterilised and sterilisation was subsequent to the specified time limit, then the decision is taken according to which the device is sterile and that it can be used.

After the sleeve/treatment device pair as described previously have been used, the RFID reader (711) in the treatment device changes the information in the sterilisation sleeve's (150) RFID component (151) indicating that the sleeve has been used and is therefore no longer sterile. In addition, if the sleeve is used subsequently without prior sterilisation, the user will be warned that the sleeve is not sterile and firing is not authorised.

Double-Blind Clinical Study/Randomized Study

In a certain context, the RFID reader and safety strip unit can also be used for carrying out a so-called "double-blind" clinical study. In addition to containing the laser parameters, the strip contains information stipulating whether the laser should actually fire or simply simulate firing. The treatment device is designed so that whether it actually treats the area to be treated or not, the same behaviour is perceptible to the practitioner (emits a sound or a visual signal indicating firing) . The strips are programmed during manufacture by software that randomly authorises "actual" treatment or not via parameters contained in the strip's RFID component.

This same software is able to read information concerning treatment authorisation. The practitioner therefore treats the patient using the strip without knowing whether the treatment is actually delivered by the treatment device. After using the strip, the practitioner hands the strip over to whoever is responsible for the clinical study with his/her assessment of the results of treatment. The person responsible for the study then reads the strip in order to determine whether the patient has been treated or not.

Thus, with such a process, no direct participant can know when the device provides actual treatment or when it doesn't during the clinical trial. This principle ensures that opinions with regard to the results of treatment collected are obtained with complete objectivity.

The invention claimed is:

1. A dermatological treatment device comprising an energy source, the energy source emitting a quasi-Gaussian laser beam, a means of shaping the beam between the energy source and the zone to be treated, the means of shaping being suitable for converting the beam into a beam with a flat-top profile having a power distributed homogeneously over a given area, and a detachable and interchangeable optical unit.

2. The treatment device as claimed in claim 1, wherein the means used to shape the laser beam (61) includes at least one lens array (64) and one cylindrical lens (66).

3. The treatment device as claimed in claim 1, further comprising an optical fibre (63) placed in front of the energy source (62) in order to reduce the divergence of the energy source (62) fast axis.

4. The treatment device as claimed in claim 1, further comprising a means of pyrometry (712).

5. The treatment device as claimed in claim 1, further comprising a user interface including at least one of the following components: an LCD screen (75), an emergency stop button (76), a on/off button (77), a double button system (88), an indicator light (89) and a buzzer (717).

6. The treatment device as claimed in claim 1, wherein the energy source is a diode (62) the wavelength of which is between 800 nm and 1800 nm.

7. The treatment device as claimed in claim 1, further comprising a battery system (71) for autonomous operation.

8. The treatment device as claimed in claim 1, further comprising an RFID reader (711) in order to ensure the treatment device can be safely used.

9. The treatment device as claimed in claim 8, wherein the range of the RFID reader is less than 5 mm.

10. The treatment device as claimed in claim 1, further comprising a microcontroller (111) for managing the energy source.

11. The treatment device as claimed in claim 1, further comprising a recess (83), positioned downstream of the laser beam shaper output in order to ensure there is a distance between the shaper output and the treatment zone.

12. A treatment apparatus comprising a treatment device as claimed in claim 1, wherein said treatment device further comprises a sterilisation sleeve (80).

13. The treatment apparatus as claimed in claim 12, wherein the treatment device further comprises an RFID component (151) included in the sterilisation sleeve (80).

14. A dermatological treatment equipment comprising a treatment device as claimed in claim 1 and an RFID component, wherein the RFID component (92) is designed to transmit information about the treatment zone to the treatment device.

15. The dermatological treatment equipment as claimed in claim 14, wherein the treatment device further comprises a microcontroller (112) for managing reading of the RFID component (92).

16. The dermatological treatment equipment as claimed in claim 14, wherein the RFID component (92) interacts with the energy source by means of a contact.

17. The dermatological treatment equipment as claimed in claim 14, wherein the energy source operating settings are memorised in the RFID component (92) and communicated to the energy source control device.

18. The dermatological treatment equipment as claimed in claim 14, wherein the RFID component (92) operates at a frequency of between 13 and 14 MHz.

19. The dermatological treatment equipment as claimed in claim 14, wherein the RFID component (92) comprises a means of storing information characterising a status of the area to be treated, the information corresponding to a status selected from the group consisting of:
    the area to be treated has not been treated;
    the area to be treated is in the course of treatment; and
    treatment of the area to be treated has finished.

20. The dermatological treatment equipment as claimed in claim 14, wherein the treatment device, upon receiving information about the status of the zone to be treated, includes the means of preventing reuse of any adhesive attachment element containing an RFID component (92) which has already been used once to treat the treatment zone.

21. The dermatological treatment equipment as claimed in claim 14, wherein the RFID (92) component is contained in an adhesive element (90), the adhesive element (90) being positioned close to the area to be treated.

22. The dermatological treatment equipment as claimed in claim 21, wherein the RFID component (92) includes means to prevent reuse of any adhesive attachment element (90) which has already been used to treat a treatment zone.

23. A treatment unit, comprising an apparatus as defined in claim 12 and the treatment device includes an RFID reader (711).

24. A process for using the treatment unit according to claim 23 comprising the steps of:
    querying by the RFID reader (711) of the treatment device of the RFID component (151) of the sterlising sleeve (150) in order to obtain information characterising the state of sterilisation of the sleeve and/or the last date of sterilization of the sleeve;
    deciding on the basis of the obtained information as whether the sleeve can be used or not; and
    authorising the device to fire or not according to the deciding step.

25. The process according to claim 24, further comprising the step of:
    once use of the device finishes, changing the information in the RFID component by the RFID reader (711) so as to prevent the sleeve being used again without sterilisation.

* * * * *